(12) United States Patent
Burchesky et al.

(10) Patent No.: US 10,670,490 B2
(45) Date of Patent: Jun. 2, 2020

(54) MEASUREMENT SYSTEM AND METHOD THEREFORE

(71) Applicant: GE HEALTHCARE BIO-SCIENCES CORP., Marlborough, MA (US)

(72) Inventors: Robert Douglas Burchesky, Westborough, MA (US); James Molloy, Westborough, MA (US)

(73) Assignee: GE Healthcare Bio-Sciences Corp., Marlborough, MA (US)

(*) Notice: Subject to any disclaimer, the term of this patent is extended or adjusted under 35 U.S.C. 154(b) by 262 days.

(21) Appl. No.: 15/824,045

(22) Filed: Nov. 28, 2017

(65) Prior Publication Data

US 2019/0162627 A1    May 30, 2019

(51) Int. Cl.
| | | |
|---|---|---|
| G01M 3/32 | (2006.01) | |
| C12M 1/34 | (2006.01) | |
| G01M 3/00 | (2006.01) | |
| C12M 1/00 | (2006.01) | |
| G01G 17/04 | (2006.01) | |

(52) U.S. Cl.
CPC .......... G01M 3/3218 (2013.01); C12M 23/14 (2013.01); C12M 41/12 (2013.01); C12M 41/40 (2013.01); G01M 3/007 (2013.01); G01G 17/04 (2013.01)

(58) Field of Classification Search
CPC ............................. G01M 3/007; G01M 3/3218
See application file for complete search history.

(56) References Cited

U.S. PATENT DOCUMENTS 9,534,980 B2    1/2017  Dahlberg et al.
2008/0213874 A1*  9/2008  Mitchell ................ G01F 23/14
                                                          435/287.1

FOREIGN PATENT DOCUMENTS

CN        104776988 A      7/2015
WO        2008/106193 A1   9/2008

OTHER PUBLICATIONS

PCT International Search Report and Written Opinion for PCT Application No. PCT/EP2018/082478 dated Mar. 1, 2019 (15 pages).

* cited by examiner

Primary Examiner — Leslie J Evanisko
Assistant Examiner — Leo T Hinze
(74) Attorney, Agent, or Firm — Eversheds Sutherland (US) LLP

(57) ABSTRACT

The present invention relates to a method for a measurement system configured to test a flexible bio-process bag, the method comprising providing at least one flexible bio-process bag having a volume, wherein the at least one flexible bio-process bag is initially filled with a gas and inflated to a reference pressure (Pu), obtaining a leak model, obtaining baseline information, wherein the baseline information comprises at least a weighed first mass value ($m_{baseline}$) and a first time value ($t_1$), obtaining evaluation information, wherein the evaluation information comprises at least a weighed second mass value ($m_{evaluation}$) and a second time value ($t_2$), testing the flexible bio-process bag based on the leak model, the baseline information and the evaluation information.

11 Claims, 6 Drawing Sheets

Eq. (1): $q_m = \frac{\Delta m}{\Delta t} \approx (C_d \epsilon)(\frac{\pi}{4}d^2)\sqrt{\frac{2M}{RT}}\sqrt{p_{u,0}(p_{u,0} - p_{d,a})}$ Definitions:

| Symbol | Name | SI Units | Value (if constant) |
|---|---|---|---|
| $q_m$ | Steady-State Mass Flow Rate | $kg/s$ | |
| $\Delta m$ | Mass Loss for Full Leak Test Duration | $kg$ | |
| $\Delta t$ | Leak Test Duration | $s$ | |
| $C_d$ | Discharge Coefficient for a Sharp-Edged Orifice | | 0.6 |
| $\epsilon$ | Expansibility Factor (5-10kPa Overpressure, 10-500μm Orifice) | | 1 |
| $d$ | Orifice Diameter | $m$ | |
| $M$ | Molal Mass of Air | $kg \cdot mol^{-1}$ | 0.0289644 |
| $R$ | Ideal Gas Constant | $J \cdot mol^{-1} \cdot K^{-1}$ | 8.3144598 |
| $T$ | Ambient Lab Temperature | $K$ | |
| $p_{u,0}$ | Initial Pressure in Cellbag (Upstream of Orifice) | $Pa$ | |
| $p_{d,a}$ | Ambient Lab Pressure (Downstream of Orifice) | $Pa$ | |

Fig. 5

MEASUREMENT SYSTEM AND METHOD THEREFORE

TECHNICAL FIELD

The present invention relates to a measurement system configured to test a flexible bio-process bag and a method therefore.

BACKGROUND

Various processes use fluid provided in flexible bio-process bags, e.g. a cellbag or other single-use bio reactor, a cell culture media bag or a single-use mixer bag. Before filling the flexible bio-process bag with fluid, the flexible bio-process bag is tested for leaks and optionally provided with a certificate. A flexible bio-process bag having a leak exceeding a certain diameter may be tested as unusable.

Conventional measurement systems for testing flexible bio-process bags typically inflates the flexible bio-process bag with a fluid, such as air, and fills it up to a reference pressure. The pressure of the flexible bio-process bag is then monitored over a predetermined time period. The flexible bio-process bag is then tested as unusable if the pressure after the predetermined time period has fallen below a test threshold and classified as usable if the monitored pressure is equal to or above the test threshold.

A drawback with such conventional systems is that the measurements are sensitive to air pressure variations in the surrounding environment, such as changing weather or opening or closing of doors or windows. A further drawback is that the tests are time consuming, especially when testing for small leaks. A further drawback is that the accuracy is low. Yet a further drawback is that only one flexible bio-process bag at a time can be tested. Yet a further drawback is that such tests are only valid for a particular flexible bio-process bag volume. Yet a further drawback is that such tests are sensitive to membrane creep.

Thus, there is a need for an improved measurement system and method thereof.

OBJECTS OF THE INVENTION

An objective of embodiments of the present invention is to provide a solution which mitigates or solves the drawbacks and problems described above.

SUMMARY OF THE INVENTION

The above and further objectives are achieved by the subject matter described herein. Further advantageous implementation forms of the invention are further defined herein According to a first aspect of the invention, the above mentioned and other objectives are achieved with a method for a measurement system configured to test a flexible bio-process bag. The method comprises providing at least one flexible bio-process bag having a volume. The at least one flexible bio-process bag is initially filled with a gas and inflated to a reference pressure. The method further comprises obtaining a leak model. The method further comprises obtaining baseline information. The baseline information comprises at least a weighed first mass value and a first time value. The method further comprises obtaining evaluation information, wherein the evaluation information comprises at least a weighed second mass value and a second time value. The method further comprises testing the flexible bio-process bag based on the leak model, the baseline information and the evaluation information.

At least an advantage of the invention according to this embodiment is that the measurements are not sensitive to air pressure variations in the surrounding environment, as the weight of the bag remains constant when the air pressure varies. A further advantage is that the proposed method saves time as the weight can be determined with better accuracy than by using a pressure based method, especially if testing for small leaks. Yet an advantage is that test time is reduced as multiple flexible bio-process bags at a time can be tested. Yet an advantage is that the method can be performed independently of flexible bio-process bag volume. Yet an advantage is that the test method is insensitive to membrane creep.

According to a second aspect of the invention, the above mentioned and other objectives are achieved with a measurement system configured to test the flexible bio-process bag. The system comprising a scale configured to receive at least one flexible bio-process bag and to provide mass values indicative of the weight of the at least one flexible bio-process bag, a control unit comprising a processor and a memory, said memory containing instructions executable by said processor, whereby said measurement system is operative to perform the method according to the first aspect.

The advantages of the second aspect are the same as for the first aspect.

Further applications and advantages of embodiments of the invention will be apparent from the following detailed description.

BRIEF DESCRIPTION OF THE DRAWINGS

FIG. 5 shows an example of a leak model according to one or more embodiments of the present disclosure.

Figure 1:
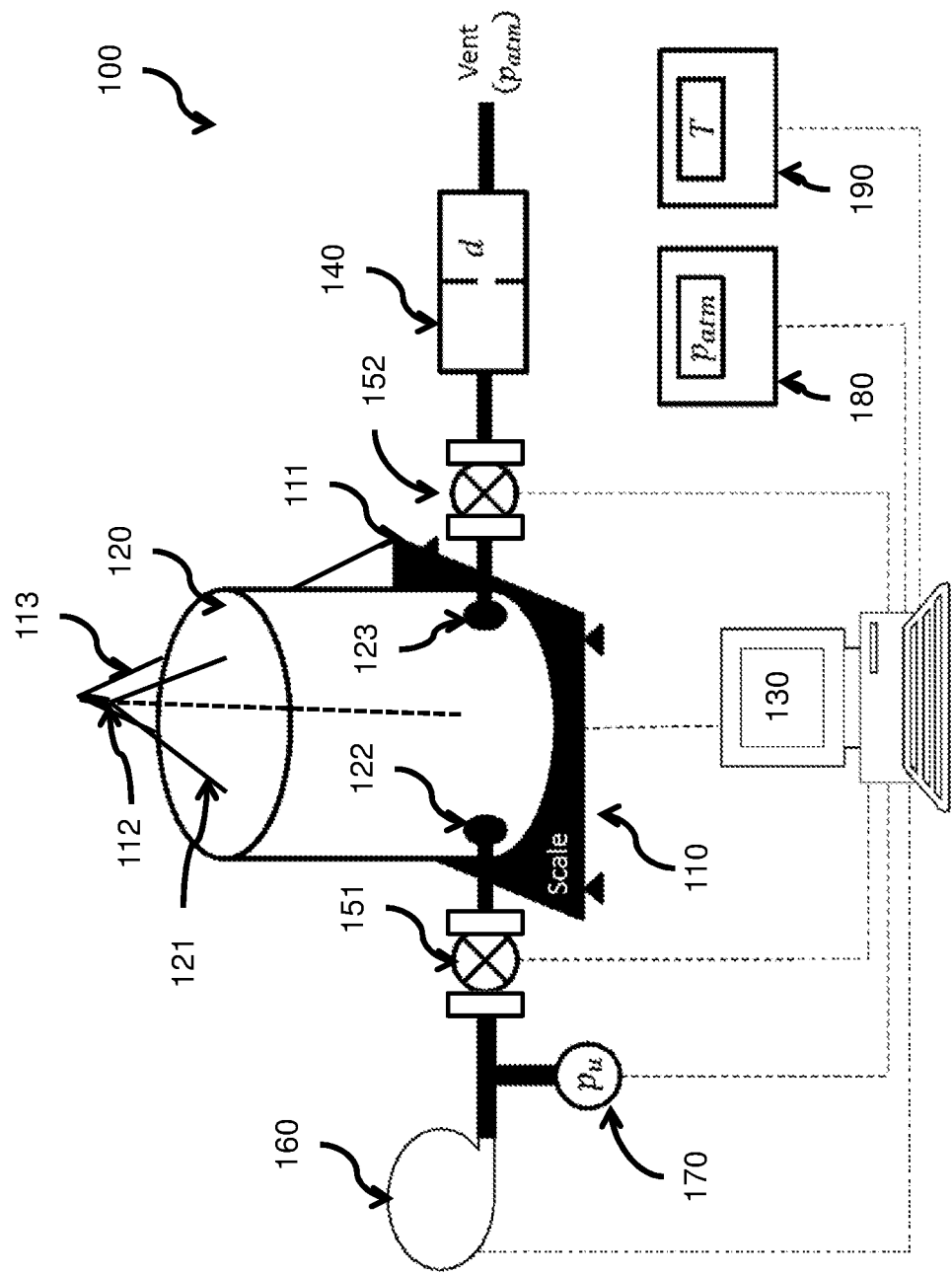
FIG. 1 shows a measurement system according to one or more embodiments of the present disclosure.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

DETAILED DESCRIPTION

An "or" in this description and the corresponding claims is to be understood as a mathematical OR which covers "and" and "or", and is not to be understand as an XOR (exclusive OR). The indefinite article "a" in this disclosure and claims is not limited to "one" and can also be understood as "one or more", i.e., plural.

In the present disclosure reference will be made interchangeably to flexible bio-process bag and cellbag.

A physics model for cellbag leak detection using mass loss measurements obtained by gravimetric methods is disclosed herein. The advantages of the present disclosure involves a resulting leak model which is independent of flexible bio-process bag volume and is not affected by flexible bio-process bag membrane creep. The mass loss through the small leak is directly proportional to the time period of the test duration, the square of the leak diameter, the square root of the initial inflation pressure and the square root of the initial pressure drop across the leak. It is also inversely proportional to the square root of the absolute temperature. Plots of mass loss v. test time from a 75 μm leak for different cellbag volumes and a range of inflation pressures are provided in FIG. 6. In one example, the 20 in$H_2O$ inflation pressure (1 in$H_2O$=249.1 Pa) mass loss curve hits the detection limit after 34 seconds and a likely resolution limit at 102 seconds, thus establishing competitiveness with pressure decay leak detection.

Monte Carlo analysis was used to quantify the effects of expected ambient pressure and temperature variation in a bag manufacturing cleanroom. For ambient gage pressure variation of 0.09±0.04 in$H_2O$ and ambient temperature variation of 68±3° F., the variation in the mass loss prediction is only ±0.3%, showing that the disclosed method is robust to normal variation in environmental conditions.

The leak model provides the transfer function and a calibration procedure fits the leak model to the specific test design. Two methods of performing the calibration procedure are discussed herein. First, simple linear regression can be used to create a calibration line from mass loss v. time data generated using a single leak standard such as an orifice leak, leak master or Brooks valve. Second, design of experiments can be used to organize leak experiments from multiple standards and inflation pressures. The model equation can be linearized using a logarithm transform and the whole experiment can be reduced using multiple regression of the transformed data. This method enables design of a precise leak sizing process and creation of new consumable offerings for customers interested in guaranteed maximum leak sizes to minimize risk of batch loss or contamination for critical drug development processes. Implementation depends on shock, vibration and draft controls.

The formula for the mass loss curve for a cellbag with a leak according to the present disclosure is presented as Eq. (2.1), $$\Delta m \approx \Delta t (C_d \epsilon)(\frac{\pi}{4}d^2)\sqrt{p_{u,o}}\sqrt{p_{u,o} - p_{atm}}\sqrt{\frac{2M}{RT}}, \quad (2.1)$$

where $\Delta m$ is the air mass lost by the cellbag through the leak during the elapsed test time $\Delta t$, Cd is the coefficient of discharge determined by orifice geometry, $\epsilon$ is the expansibility factor that corrects the equation for the compressibility of air, d is the diameter of the leak, pu,0 is the inflation pressure of the cellbag at $t_1$=0 upstream of the leak,1 M is the molal mass of air, R is the ideal gas constant, T is the absolute temperature of the air in the cellbag and patm is the ambient pressure of the laboratory into which the leak vents. MKS units are used consistently for all calculations in this paper to prevent errors.

Figure 6:
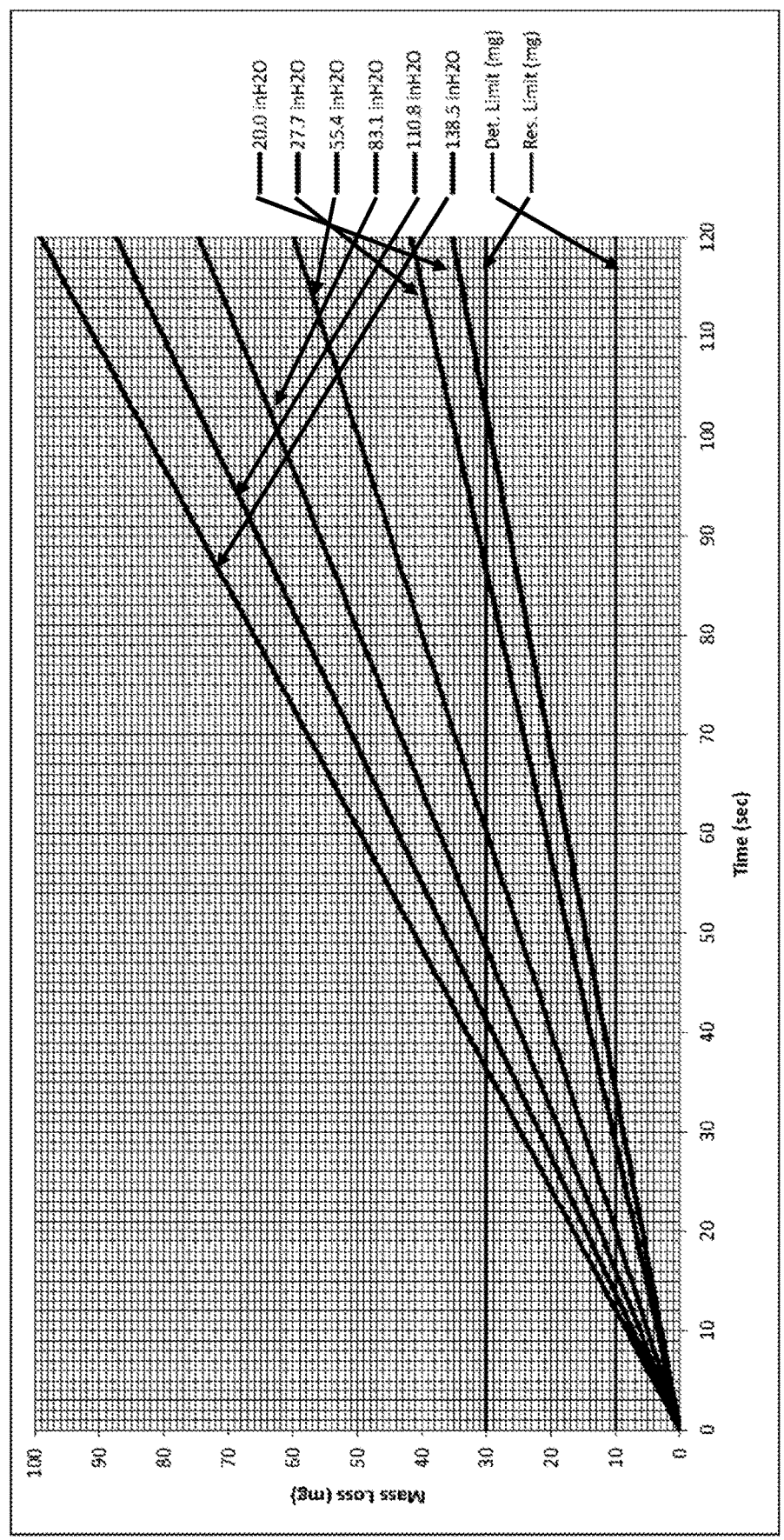
FIG. 6 shows an example of a leak model in the form of mass loss curves according to one or more embodiments of the present disclosure.

FIG. 6 shows an example of a leak model in the form of mass loss curves according to one or more embodiments of the present disclosure. The leak model is applicable to cellbags of any volume, for a 75 μm diameter orifice leak and a laboratory temperature of 68° F. At the inflation pressure for the pressure decay leak tests (20 in$H_2O$), the mass loss equals the scale's detection limit of 10 mg after 34 seconds and reaches the probable resolution limit of 30 mg after 102 seconds. So, gravimetric measurement of mass loss can detect fine leaks at least as quickly as or quicker than pressure based decay leak tests.

Since Eq. (2.1) is independent of cellbag volume, a mass loss-based leak test will not be affected by creep in the cellbag membrane and the attendant volume change. Only fluctuations in cellbag air temperature and ambient pressure matter because these fluctuations change the steady-state mass flow rate; hence, the integrated mass loss Monte Carlo analysis can be applied to Eq. (2.1) to estimate the effects of temperature and ambient pressure fluctuation. For an initial inflation pressure of 20 inH2O (106301.8 Pa) and a 75 μm leak, application of example data transforms Eq. (2.1) into $$\Delta m = (2.324270651 \times 10^{-5})\frac{\Delta t}{\sqrt{T}}\sqrt{1 - \frac{P_{atm}}{106301.8}}, \quad (3.1)$$

where all constants and variables are in MKS units. The cleanroom may have an average gage pressure of 0.09 inH2O (101347.4 Pa) with a variation range of ±0.04 inH2O. Therefore, one can model ambient pressure with a uniform distribution with a minimum of 0.05 inH2O (101337.4 Pa) and a maximum of 0.13 in$H_2O$ (101357.3 Pa). The cleanroom temperature range is 68±3° F. Similarly, one can model ambient temperature with a uniform distribution with a minimum of 65° F. (291.5K) and a maximum of 71° F. (294.8K).

FIG. 6 shows that at $t_2$=60 s, the expected or modelled mass loss $\Delta m_{model}$ is 18 mg. Correcting for the positive pressure in the cleanroom, the model predicts a nominal mass loss of 17.6 mg, merely 2% smaller than the result from taking ambient pressure as the nominal value of atmospheric pressure near sea level.

The results of a performed Monte Carlo analysis based on Eq. (3.1) using 10,000 trials drawn from the assumed ambient pressure and temperature distributions above was performed. The results show that the mean mass loss is 17.58 mg, which is within 0.1% of the predicted value. The span of mass loss under expected ambient pressure and temperature variation is 0.11 mg, or ±0.3% of the mean mass loss value. The standard deviation from the Monte Carlo analysis is s$\Delta m$=0.03 mg. Thus, the mass loss leak detection method descried herein should be robust under normal cleanroom environmental fluctuations. Sensitivity analysis shows that temperature variation explains 90% of the mass loss variance and ambient pressure variation explains the remaining 10%. Therefore, improved temperature control is the lever to throw should there ever be a variance problem.

FIG. 1 shows a measurement system 100 according to one or more embodiments of the present disclosure. The measurement system 100 comprises a scale 110 configured to receive at least one flexible bio-process bag 120 and to provide mass values or weighed mass values indicative of the weight of the at least one flexible bio-process bag 120. The measurement system 100 further comprises a control unit 130 configured to provide a test result indicative of if the flexible bio-process bag 120 is usable or unusable. A more detailed description of the control unit 130 is provided in relation to FIG. 2. The control unit 130 is communicatively coupled to the scale 110 and may further be configured to receive the mass values indicative of the weight of the at least one flexible bio-process bag 120, e.g. in the form of mass values comprised in a control signal.

The scale 110 may in embodiments comprise a platform 111 configured to receive a load to be measured by the scale 100 and typically arranged along a plane, e.g. arranged to extend in a flat horizontal plane. The scale 110 may in embodiments further comprise a receiving arrangement 112, e.g. a hook, which is suspended along a normal of the plane extending from a center point of the platform. The receiving arrangement 112 is configured to attach to a grip 121 of the flexible bio-process bag, e.g. to extend through a handle of the bag, the grip 121 typically arranged at one end or side of the flexible bio-process bag 120. In one example, the grip 121 is shaped like a carrying handle that can be used by an operator or robot to carry the bag. The receiving arrangement 112 may e.g. be suspended by a rack or cradle, e.g. attached to the scale 110 and/or platform 111 or may be arranged as a separate unit.

The measurement system 100 may in embodiments further comprise an orifice plate 140 having an orifice of a predetermined diameter d and configured to allow fluid received from a plate inlet pass through the orifice to a plate outlet.

The measurement system 100 may in embodiments further comprise an input valve 151 configured to control the flow of compressed gas received from an inlet coupled/couplable to a gas source 160 to an outlet coupled/couplable to an input port 122 of the flexible bio-process bag 120 in response to receiving a first control signal. The control signal is typically received from the control unit 130 and may be any suitable control signal such as a serial signal from a Universal Serial Bus, USB, port.

The measurement system 100 may in embodiments further comprise an output valve 152 configured to control the flow of gas from an inlet coupled/couplable to an output port 123 of the flexible bio-process bag 120 to an outlet coupled/couplable to the orifice plate 140 in response to receiving a second control signal.

The measurement system 100 may in embodiments further comprise a barometer or environment pressure sensor 180 configured to measure air pressure of the environment of the measurement system, e.g. air pressure in a lab, as an air pressure value/s and send the air pressure value/s comprised in a third control signal to the control unit 130.

The measurement system 100 may in embodiments further comprise a temperature sensor 190 configured to measure ambient or environment temperature of the environment of the measurement system, e.g. ambient temperature in a lab, as an ambient temperature value/s and send the ambient temperature value/s comprised in a fourth control signal to the control unit 130.

The control unit 130 is communicatively coupled to a selection of any of the input valve 151, the output valve 152, the gas source 160, the reference pressure sensor 170, the barometer 180 and the temperature sensor 190.

In an embodiment, the control unit 130 comprises a processor and a memory, the memory contains instructions executable by the processor, whereby said measurement system is operative to perform the method described herein.

Figure 2:
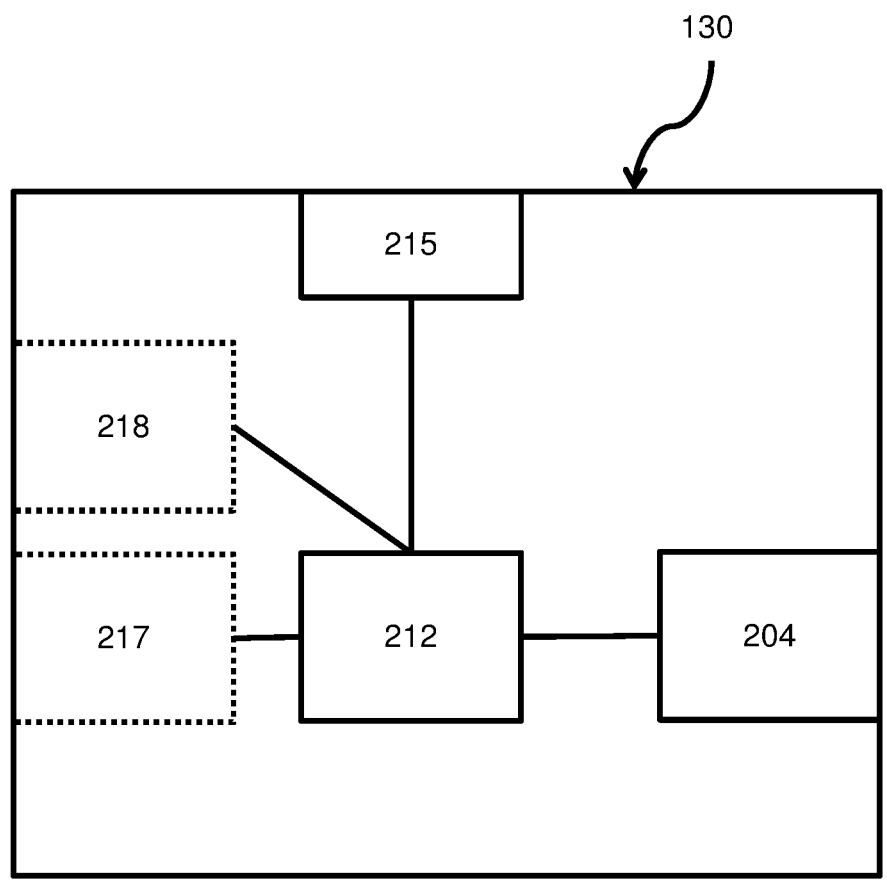
FIG. 2 shows a control unit comprised in the measurement system according to one or more embodiments of the present disclosure.

FIG. 2 shows the control unit 130 according to one or more embodiments of the present invention. The control unit 130 may be in the form of e.g. an Electronic Control Unit, a server, an on-board computer, a stationary computing device, a laptop computer, a tablet computer, a handheld computer, a wrist-worn computer, a smart watch, a smartphone or a smart TV. The control unit 130 may comprise a processor 212 communicatively coupled to an optional transceiver 204 configured for wired or wireless communication. The control unit 130 may further comprise at least one optional antenna (not shown in figure). The antenna may be coupled to the transceiver 204 and is configured to transmit and/or emit and/or receive wired or wireless signals in a communication network, such as a serial signal, WiFi, Bluetooth, 3G, 4G, 5G etc. In one example, the processor 212 may be any of a selection of processing circuitry and/or a central processing unit and/or processor modules and/or multiple processors configured to cooperate with each-other. Further, the control unit 130 may further comprise a memory 215. The memory 215 may e.g. comprise a selection of a hard RAM, disk drive, a floppy disk drive, a flash drive or other removable or fixed media drive or any other suitable memory known in the art. The memory 215 may contain instructions executable by the processor to perform any of the steps or methods described herein. The processor 212 may further be communicatively coupled to a selection of any of the transceiver 204, the memory 215, the input valve 151, the output valve 152, the gas source 160, the reference pressure sensor 170, the barometer 180 and the temperature sensor 190. The control unit 130 may be configured to send/receive control signals directly to any of the above mentioned units or to external nodes or to send/receive control signals via the wired and/or wireless communications network.

The wired/wireless transceiver 204 and/or a wired/wireless communications network adapter may be configured to send and/or receive data values or parameters as a signal to or from the processor 212 to or from other external nodes. E.g. data values or parameters indicative of measured weight, temperature or pressure values.

In one or more embodiments, the control unit 130 may further comprise an input device 217, configured to receive input or indications from a user and send a user input signal indicative of the user input or indications to the processing means 212. In one or more embodiments the control unit 130 may further comprise a display 218 configured to receive a display signal indicative of rendered objects, such as text or graphical user input objects, from the processing means 212 and to display the received signal as objects, such as text or graphical user input objects, e.g. in the form of a screen or virtual reality, VR, interface such as VR goggles. In one embodiment the display 218 is integrated with the user input device 217, e.g. in the form of a touchscreen or virtual reality interface, and is configured to receive a display signal indicative of rendered objects, such as text or graphical user input objects, from the processing means 212 and to display the received signal as objects, such as text or graphical user input objects, and/or configured to receive input or indications from a user and send a user-input signal indicative of the user input or indications to the processing means 212. In one or more embodiments, the processing means 212 is further communicatively coupled to the input device 217 and/or the display 218 and/or the additional sensors.

In a further embodiment, the control unit 130 may further comprise and/or be coupled to one or more additional sensors (not shown in the figure) configured to receive and/or obtain and/or measure physical properties pertaining to the measurement system 100 and send one or more sensor signals indicative of the physical properties to the processing means 212.

Figure 3:
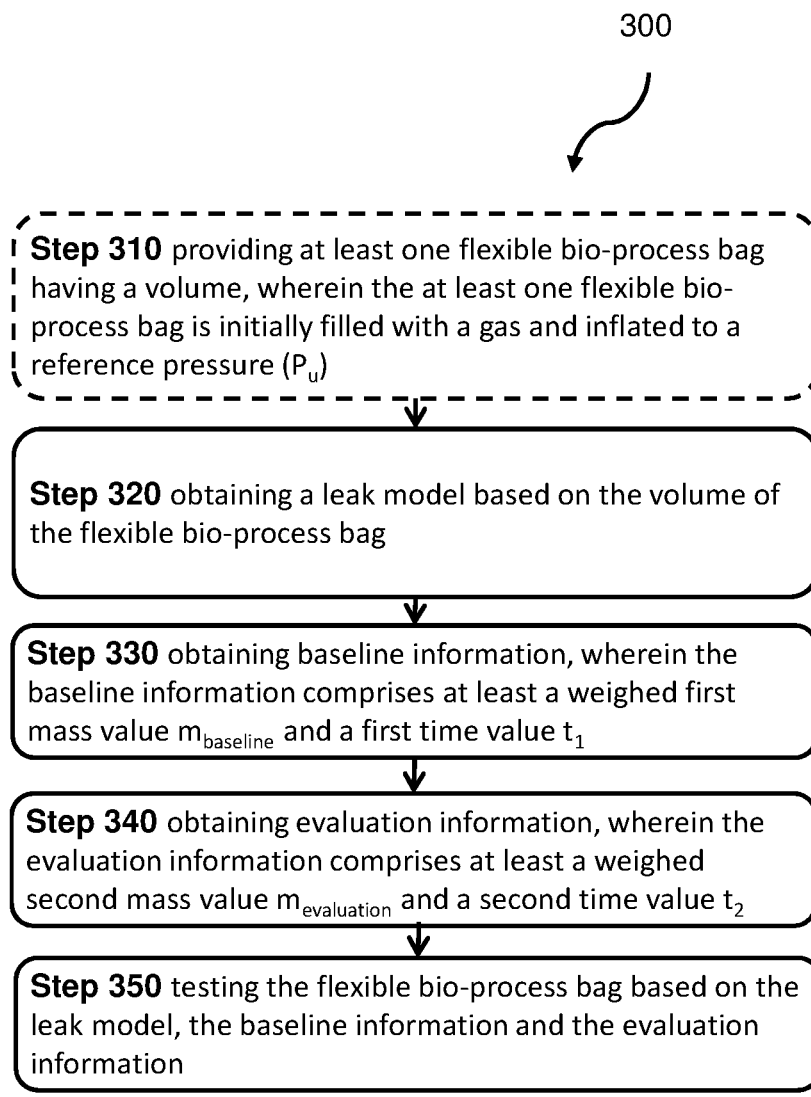
FIG. 3 shows a method for a measurement system according to one or more embodiments of the present disclosure.

FIG. 3 shows a method 300 for a measurement system according to one or more embodiments of the present disclosure. The measurement system configured to test a flexible bio-process bag, the method comprising:

OPTIONAL STEP 310: providing at least one flexible bio-process bag 120 having a predetermined volume, wherein the at least one flexible bio-process bag 120 is initially filled with a gas and inflated to a reference pressure $P_u$. The at least one flexible bio-process bag 120 may e.g. be provided by attaching the flexible bio-process bag 120 to the receiving arrangement 112. The gas can be air, but it can also be another gas or gas mixture, having either a higher or a lower density than air, e.g. nitrogen or helium (lower density), argon or carbon dioxide (higher density).

STEP 320: obtaining a leak model. The leak model may be obtained by retrieving it from memory, by performing a calibration procedure or by receiving or retrieving the leak model from other external nodes.

STEP 330 obtaining baseline information, wherein the baseline information comprises at least a weighed first mass value $m_{baseline}$ and a first time value $t_1$. The first mass value $m_{baseline}$ is typically indicative of the weight of the provided at least one flexible bio-process bag having a predetermined volume and being initially filled with a gas and inflated to a reference pressure $P_u$ at a time equal to the first time value $t_1$. The baseline information may be obtained by retrieving it from memory, by retrieving weighed and recorded mass values from the scale 110 or by receiving or retrieving the baseline information from other external nodes.

STEP 340: obtaining evaluation information, wherein the evaluation information comprises at least a weighed second mass value $m_{evaluation}$ and a second time value $t_2$. The second mass value $m_{evaluation}$ is typically indicative of the weight of the provided at least one flexible bio-process having a test pressure $P_{test}$ at a time equal to the second time value $t_2$. The evaluation information may be obtained by retrieving it from memory, by retrieving weighed and recorded mass values from the scale 110 or by receiving or retrieving the evaluation information from other external nodes.

STEP 350: testing the flexible bio-process bag based on the leak model, the baseline information and the evaluation information. In one example, testing comprises comparing the results of the leak model, after providing a selection of the first time value $t_1$ and the second time value $t_2$, with an absolute value of a difference between the first mass value value $m_{baseline}$ and the second mass value $m_{evaluation}$. If the absolute value of the difference is less than or equal to the mass value indicated by the results of the leak model, a test result indicative of the at least one flexible bio-process bag 120 being usable is generated. If the absolute value of the difference is greater than the mass value indicated by the results of the leak model, a test result indicative of the at least one flexible bio-process bag 120 being unusable is generated.

In an example, the method is performed by the processor 212 of the control unit 130. An operator has initially provided at least one flexible bio-process bag 120 having a predetermined volume, e.g. by attaching the bag to the receiving arrangement 112. The control unit 130 obtains a leak model, e.g. from the memory 215. The control unit 130 then obtains baseline information by receiving control signals comprising one or more weighed mass values from the scale 120. The baseline information comprises at least a weighed first mass value $m_{baseline}$ and/or a first time value $t_1$. The control unit 130 then obtains evaluation information by receiving control signals comprising one or more weighed mass values from the scale 120. The evaluation information comprises at least a weighed second mass value $m_{evaluation}$ and/or a second time value $t_2$. The control unit 130 then tests the provided flexible bio-process bag based on the obtained leak model, the obtained baseline information and the obtained evaluation information by comparing the results of the leak model, after providing a selection of the first time value $t_1$ and the second time value $t_2$, with an absolute value of a difference between the first mass value $m_{baseline}$ and the second mass value $m_{evaluation}$. If the absolute value of the difference is less than or equal to the mass value indicated by the results of the leak model, a test result indicative of the at least one flexible bio-process bag 120 being usable may further be generated. If the absolute value of the difference is greater than the mass value indicated by the results of the leak model, a test result indicative of the at least one flexible bio-process bag 120 being unusable is generated.

In an embodiment, the leak model is at least indicative of a first leaked mass $\Delta m_{model}$ dependent on a first time period $\Delta t_{model}$. The first mass value $m_{baseline}$ is indicative of a first weight of the flexible bio-process weighed at a point in time indicated by the first time value $t_1$. The second mass value $m_{evaluation}$ is indicative of a second weight of the flexible bio-process bag weighed at a subsequent point in time indicated by the second time value $t_2$. The first time period $\Delta t_{model}$ may be derived as an absolute value of a difference between the second time value $t_2$ and the first time value $t_1$. Testing may then be performed by determining a second leaked mass $\Delta m_{weighed}$ as the absolute value of a difference between the first mass value $m_{baseline}$ and the second mass value $m_{evaluation}$, and testing the flexible bio-process bag as usable if the second leaked mass $\Delta m_{weighed}$ is less or equal to the first leaked mass $\Delta m_{model}$ or testing the flexible bio-process bag as unusable if the second leaked mass $\Delta m_{weighed}$ is greater than the first leaked mass $\Delta m_{model}$.

In an embodiment, the leak model indicates the first leaked mass $\Delta m_{model}$ based on a relation, such as a linear or straight line equation $\Delta m_{model} = k * \Delta t_{model} + b$, wherein k is a calibration constant and b is a bias constant.

In an embodiment, the calibration constant k is determined by performing a calibration procedure involving linear regression on a set of reference data. In one example, performing a calibration procedure involves repeating STEP 310-340 multiple times for the flexible bio-process bags having the same or identical volume. In a further example, performing a calibration procedure involves repeating STEP 310-340 multiple times for the flexible bio-process bags having different volumes, e.g. 1 liter, 5 liter, 10 liter etc. The calibration procedure is further described in relation to FIG. 5.

In an embodiment, the reference data is obtained by weighing a plurality of reference flexible bio-process bags having the predetermined volume, being initially filled with a gas and inflated to a reference pressure Pu and having a known mass leak rate, e.g. by using an orifice plate.

In an embodiment, the at least one flexible bio-process bag is initially inflated to a reference pressure Pref, e.g. 1-10 atm.

Figure 4:
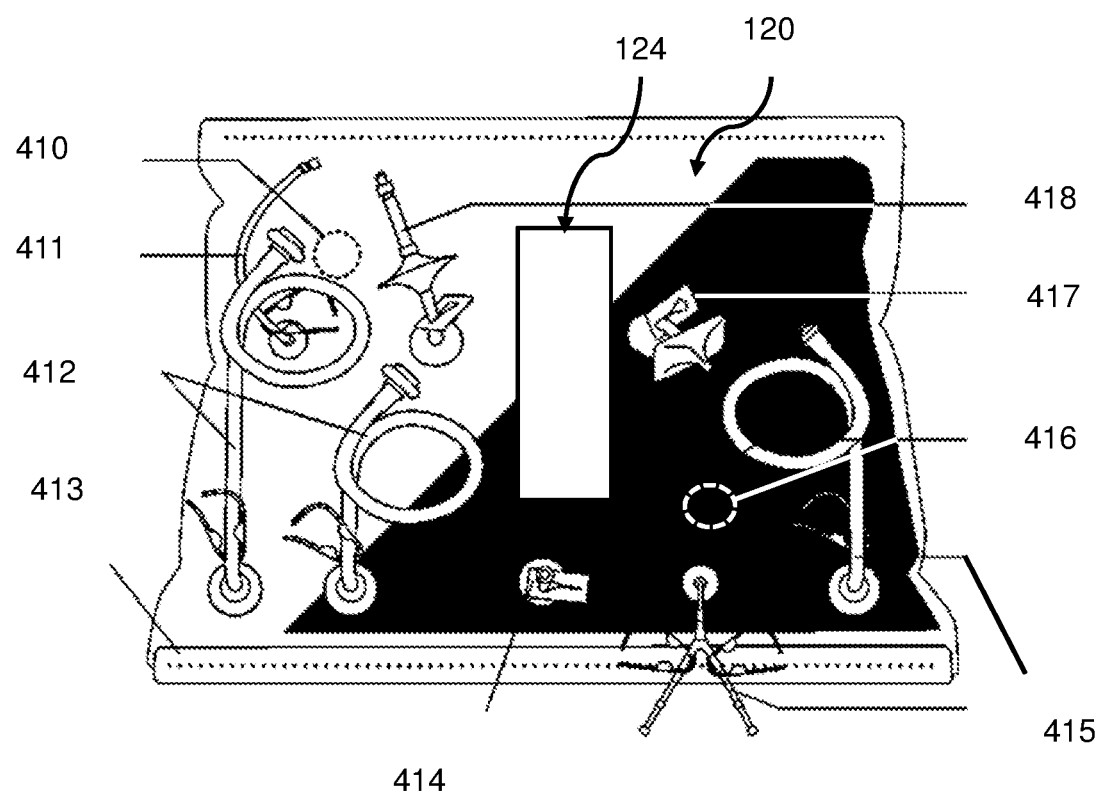
FIG. 4 shows a flexible bio-process bag provided with a test certificate according to one or more embodiments of the present disclosure.

FIG. 4 shows a flexible bio-process bag 120 provided with a test certificate 124 according to one or more embodiments of the present disclosure. The certificate shows or indicates the results of a test performed according to the method described herein, e.g. indicating that the flexible bio-process bag is usable. In an embodiment, the flexible bio-process bag is presterilized. In embodiments, the flexible bio-process bag 120 may further comprise any one of an optical Dissolved Oxygen DO sensor 410 embedded in the bag, optional tubing, inoculation/harvest lines 412, a cellbag rod 413, a needleless sampling point 414, further optional tubing 415, a pH sensor embedded in bag 416, an air inlet filter 417 and an air outlet filter 418.

FIG. 5 shows an example of a leak model according to one or more embodiments of the present disclosure.

$$q_m = \frac{\Delta m}{\Delta t} \approx (C_d \epsilon)\left(\frac{\pi}{4}d^2\right)\sqrt{\frac{2M}{RT}}\sqrt{p_{u,o}(p_{u,o} - p_{d,a})} \quad \text{Eq. (1)}$$

In an example, assumptions are made that:
ambient temperature and pressure are constant in the environment, typically a lab, during any calibration procedure and/or testing of flexible bio-process bags.
flexible bio-process bag initial inflation pressure can be set to the same value time after time.
the orifice plate used in the calibration procedure has a fixed and known diameter d, which is of a size inconsequential to any use case, e.g. an end customers' cellbag or flexible bio-process bag use cases.

After making the above assumptions, Eq. (1) can be rewritten as:

$$q_m = \frac{\Delta m}{\Delta t} \approx \text{constant} \quad \text{Eq. (2)}$$

I.e. the relation can be approximated by a line equation $\Delta m_{model} = k^* \Delta t_{model} + b$, wherein k is a calibration constant and b is a bias constant.

In an example, a calibration procedure with reference to FIG. 1 is described. A flexible bio-process bag 120 with a known volume and an orifice plate 140 with a known diameter d is provided. The flexible bio-process bag 120 is initially filled with a gas and inflated to a reference pressure $P_u$. Baseline information is then obtained comprising at least a weighed first mass value $m_{baseline}$ weighed at a first point in time $t_1$. Evaluation information is then obtained comprising at least a weighed second mass value $m_{evaluation}$ weighed at a second point in time $t_2$. A leak model for the known volume can then be obtained as a first leaked mass $\Delta m_{model}$ dependent on a first time period $\Delta t_{model}$, where $\Delta m_{model}$ is derived as absolute value ($m_{evaluation} - m_{baseline}$) and the first time period $\Delta t_{model}$ can be derived as the absolute value ($t_2 - t_1$). The calibration procedure may be repeated multiple times with the same or different flexible bio-process bags. It is further understood that the calibration procedure may be repeated for flexible bio-process bags having different volumes.

The leak model can then be used to perform a test by determining a second leaked mass $\Delta m_{weighed}$ as the absolute value of a difference between the first mass value $m_{baseline}$ and the second mass value $m_{evaluation}$. The calibration constant k can then be determined based on a quota of mass and weight. The flexible bio-process bag is tested as usable if a measured quota, i.e. the second leaked mass $\Delta m_{weighed}$ divided by the absolute value($t_2 - t_1$), is less or equal to the modeled quota or the calibration constant k, i.e. the first leaked mass $\Delta m_{model}$ and the first time period $\Delta t_{model}$. The flexible bio-process bag is then tested as unusable if the quota of the second leaked mass $\Delta m_{weighed}$ and the absolute value($t_2 - t_1$) greater than the quota of the first leaked mass $\Delta m_{model}$ and the first time period $\Delta t_{model}$.

If the flexible bio-process bag is tested as usable, it is certified to have no leak greater than or equal to the orifice size d and may be provided with a certificate indicating e.g. volume of the flexible bio-process bag, a test result as usable and the orifice size d.

A further example of a calibration procedure, with reference to a single leak standard, is described below.

Equation (2.1) can be written as a proportionality statement to highlight the key variable dependencies:

$$\Delta m \propto \frac{\Delta t d^2}{\sqrt{T}}\sqrt{p_{u,o}}\sqrt{p_{u,o} - p_{atm}}. \quad (3.2)$$

A leak master of specified flow rate or an orifice plate of known hole or orifice diameter can be used to fix d constant. The initial inflation pressure $P_{u,0}$ is fixed constant by the design of the leak test. Previously it was shown that normal fluctuations in the cellbag air temperature T and the ambient pressure $p_{atm}$ in the cleanroom produce inconsequential fluctuation in the mass loss through the leak; hence, these variables can be treated as constants. Thus, Eq. (3.2) reduces to:

$$\Delta m = k \Delta t, \quad (3.3)$$

where k is the calibration constant. The calibration procedure may proceed as follows:
1. Install or provide a cellbag, inflate the cellbag, tare the scale and open the valve to the standard leak to start the leak test.
2. Measure the mass loss at regular time intervals throughout the duration of the test.
3. Repeat Steps 1 and 2 multiple times over multiple days to capture sources of environmental and process variation.
4. Arrange the Δm v. Δt data into two columns, stacking the individual leak test runs, and perform a simple linear regression.
   a. The data should form a straight line.
   b. The R-square statistic should be 95% or greater, indicating a good fit.
   c. Per Eq. (3.3), the constant coefficient should be statistically indistinguishable from 0, as evidenced by a p-value greater than 0.05. A bias b<0 may be seen, depending on the sampling interval, because Δm=0 until the time the mass loss exceeds the detection limit.
   d. The coefficient for Δt should be statistically different from zero, as evidenced by a p-value less than or equal to 0.05. The coefficient for Δt is the calibration constant k in Eq. (3.3).
   e. The regression model residuals should follow the normal distribution and have no correlation to the model fits for Δm or to the actual values for Δt. This indicates that the model is valid and the linear fit of the data is adequate for prediction.

The calibration curve from the set of calibration leak tests is:

$$\Delta t_{test} = \frac{\Delta m_{test} - b}{k}, \quad (3.5)$$

Any cellbag producing a mass loss less than or equal to Δmtest in an elapsed time Δttest has a leak size less than or equal to that of the standard and passes the test. Since statistical software is likely to be used to perform the regression analysis, confidence intervals for predictions of Δmtest given Δttest can be used to set up the test to account for test variation. Replace Δmtest in Eq. (3.5) with its 95% lower prediction limit and recalculate Δttest. To 95% confidence, cellbags with leak sizes greater than the standard will not escape the test.

A further example of a calibration procedure, with reference to many leak standards, is described below.

Since Eq. (3.2) is a product of terms, it can be linearized using a logarithm transform. This suggests a regression equation of the form:

$$\log(\Delta m) = c_0 + c_1 \log(\Delta t) + c_2 \log(d) + c_3 \log(T) + c_4 \log(p_{u,0}) + c_5 \log(p_{u,0} - p_{atm}). \quad (3.6)$$

Get a set of leak standards and use Design of Experiments to create a factorial matrix of d and pu,0 settings. Measure the cellbag air temperature before each experimental run. Measure the environment air pressure or laboratory barometric pressure before each run and calculate the absolute ambient pressure. Run the experiments described above under the calibration procedure with reference to a single leak standard, measuring mass loss at regular time intervals for each experimental run. Use the same time intervals for each experimental run. Arrange the data in 6 columns and perform logarithm transforms on each column. Use multiple regression analysis to determine the constants c0 through c5. Perform model diagnostics as described above under the calibration procedure with reference to a single leak standard. The resulting model can be used to set leak test designs or to predict leak sizes for cellbags with unknown leak rates within the range of validity of the model.

ADVANTAGES OF THE DISCLOSURE

Mass loss measurements according to the present disclosure will not be affected by membrane creep.

The time to resolvable mass loss is short enough to compete with pressure decay methods.

The preformed Monte Carlo analysis shows that expected fluctuations in ambient temperature and pressure have very small effects on the leak rate and mass loss. Temperature variation is 9 times more significant than pressure variation.

The model is easily combined with regression analysis to create valid calibration models and precise leak sizing methods.

The chief challenges to implementation are vibration, shock and draft isolation of the product and the scale.

In embodiments, the communications network communicate use wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the control unit 130 may comprise the necessary communication capabilities in the form of e.g., functions, means, units, elements, etc., for performing the present solution. Examples of other such means, units, elements and functions are: processors, memory, buffers, control logic, mapping units, multipliers, decision units, selecting units, switches, modulators, demodulators, inputs, outputs, antennas, amplifiers, receiver units, transmitter units, power supply units, power feeders, communication interfaces, communication protocols, etc. which are suitably arranged together for performing the present solution.

Especially, the processor and/or processing means of the present disclosure may comprise one or more instances of processing circuitry, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processor" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as call processing control, user interface control, or the like.

Finally, it should be understood that the invention is not limited to the embodiments described above, but also relates to and incorporates all embodiments within the scope of the appended independent claims.

The invention claimed is:

1. Method for a measurement system configured to test a flexible bio-process bag, the method comprising:
    providing at least one flexible bio-process bag having a volume, wherein the at least one flexible bio-process bag is initially filled with a gas and inflated to a reference pressure ($P_u$),
    obtaining a leak model,
    obtaining baseline information, wherein the baseline information comprises at least a weighed first mass value ($m_{baseline}$) and a first time value ($t_1$),
    obtaining evaluation information, wherein the evaluation information comprises at least a weighed second mass value ($m_{evaluation}$) and a second time value ($t_2$), and
    testing the flexible bio-process bag based on the leak model, the baseline information and the evaluation information,
    wherein the leak model is at least indicative of a first leaked mass ($\Delta m_{model}$) dependent on a first time period ($\Delta t_{model}$), the first mass value ($m_{baseline}$) is indicative of a first weight of the flexible bio-process bag weighed at a point in time indicated by the first time value ($t_1$), the second mass value ($m_{evaluation}$) is indicative of a second weight of the flexible bio-process bag weighed at a subsequent point in time indicated by the second time value ($t_2$), wherein an absolute value of a difference between the second time value ($t_2$) and the first time value ($t_1$) equals the first time period ($\Delta t_{model}$), wherein testing is performed by:
    determining a second leaked mass ($\Delta m_{weighed}$) as the absolute value of a difference between the first mass value ($m_{baseline}$) and the second mass value ($m_{evaluation}$), and
    testing the flexible bio-process bag as usable if the second leaked mass ($\Delta m_{weighed}$) is less or equal to the first leaked mass ($\Delta m_{model}$) or testing the flexible bio-process bag as unusable if the second leaked mass ($\Delta m_{weighed}$) is greater than the first leaked mass ($\Delta m_{model}$).

2. The method according to claim 1, wherein the leak model indicates the first leaked mass ($\Delta m_{model}$) based on the relation:

$$\Delta m_{model} = k * \Delta t_{model} + b,$$

wherein k is a calibration constant and b is a bias constant.

3. The method according to claim 2, wherein the calibration constant k is determined by performing linear regression on a set of reference data.

4. The method according to claim 3, wherein the reference data is obtained by weighing a plurality of reference flexible bio-process bags having the predetermined volume, being initially filled with a gas and inflated to a reference pressure ($P_u$), and having a known mass leak rate.

5. A measurement system configured to test a flexible bio-process bag, the system comprising:
   a scale configured to receive at least one flexible bio-process bag and to provide mass values indicative of the weight of the at least one flexible bio-process bag,
   a control unit comprising:
   a processor, and
   a memory, said memory containing instructions executable by said processor, whereby said measurement system is operative to perform the method according to claim 1.

6. The measurement system according to claim 5, wherein the scale comprises:
   a platform arranged to receive a load to be measured by the scale and extending in a plane,
   a receiving arrangement suspended along a normal of the plane extending from a center point of the platform, the receiving arrangement configured to attach to a grip arranged at one end of the flexible bio-process bag.

7. Method for a measurement system configured to test a flexible bio-process bag, the method comprising:
   providing at least one flexible bio-process bag having a volume, wherein the at least one flexible bio-process bag is initially filled with a gas and inflated to a reference pressure ($P_u$),
   obtaining a leak model,
   obtaining baseline information, wherein the baseline information comprises at least a weighed first mass value ($m_{baseline}$) and a first time value ($t_1$),
   obtaining evaluation information, wherein the evaluation information comprises at least a weighed second mass value ($m_{evaluation}$) and a second time value ($t_2$), and
   testing the flexible bio-process bag based on the leak model, the baseline information and the evaluation information, further comprising:
   an orifice plate having an orifice of a predetermined diameter (d),
   an input valve configured to control the flow of compressed gas from a gas source to an input port of the flexible bio-process bag in response to receiving a first control signal, and
   an output valve configured to control the flow of gas from an output port of the flexible bio-process bag to the orifice plate in response to receiving a second control signal.

8. The method according to claim 7, further comprising a barometer configured to measure air pressure as an air pressure value and send the air pressure value comprised in a third control signal to the control unit.

9. The method according to claim 7, further comprising a temperature sensor configured to measure ambient temperature as an ambient temperature value and send the ambient temperature comprised in a fourth control signal to the control unit.

10. A measurement system configured to test a flexible bio-process bag, the system comprising:
    a scale configured to receive at least one flexible bio-process bag and to provide mass values indicative of the weight of the at least one flexible bio-process bag,
    a control unit comprising:
    a processor, and
    a memory, said memory containing instructions executable by said processor, whereby said measurement system is operative to perform the method according to claim 7.

11. The measurement system according to claim 10, wherein the scale comprises:
    a platform arranged to receive a load to be measured by the scale and extending in a plane,
    a receiving arrangement suspended along a normal of the plane extending from a center point of the platform, the receiving arrangement configured to attach to a grip arranged at one end of the flexible bio-process bag.

* * * * *